United States Patent [19]

Carol et al.

[11] 4,255,821
[45] Mar. 17, 1981

[54] ARTIFICIAL HEART PUMP

[76] Inventors: Mark P. Carol, 1902 Park Ave., Baltimore, Md. 21217; David J. Carol, 63 Scenic Dr., Leominster, Mass. 01453

[21] Appl. No.: 26,552

[22] Filed: Apr. 2, 1979

[51] Int. Cl.³ .............................................. A61F 1/00
[52] U.S. Cl. ......................................... 3/1.7; 418/36
[58] Field of Search ............. 3/1.7; 128/DIG. 3, 1 D; 418/35, 36

[56] References Cited

U.S. PATENT DOCUMENTS

| 7,751 | 11/1850 | Davis | 418/35 |
|---|---|---|---|
| 2,531,903 | 11/1950 | Berck | 418/36 |
| 3,097,366 | 7/1963 | Winchell | 3/1.7 |
| 3,430,573 | 3/1969 | Groeger | 418/36 |
| 3,541,612 | 11/1970 | Carney | 128/1 D X |
| 3,636,570 | 1/1972 | Nielson | 3/1.7 |
| 3,783,453 | 1/1974 | Bolie | 128/1 D X |
| 4,004,299 | 1/1977 | Runge | 128/1 D X |

*Primary Examiner*—Clifford D. Crowder
*Attorney, Agent, or Firm*—Clarence A. O'Brien; Harvey B. Jacobson

[57] ABSTRACT

The pump comprises two separate pumping units, one each for the systemic and pulmonary circulation systems. Each pumping unit has an outer housing enclosing a cylindrical pumping chamber. Two radially extending vanes are contained within each chamber and divide the chamber into two separate subchambers, the relative size of which varies as the vanes rotate through the pumping cycle. Pumping action is achieved when one of the vanes is held stationary while the other vane rotates. This causes one subchamber to decrease in size. This subchamber is disposed over an outlet port and the blood is forced out of that subchamber. The other subchamber is increasing in size and is disposed over an inlet port. Blood enters this inlet chamber both in a passive manner and through the suction caused by the increasing size of the subchamber. A sensor is positioned near the inlet port and measures the volume of blood entering through this port. The sensor is electrically connected to the motor which operates the pump vanes and regulates the motor speed to insure that the volumetric output of the pump is equal to the volumetric input.

18 Claims, 10 Drawing Figures

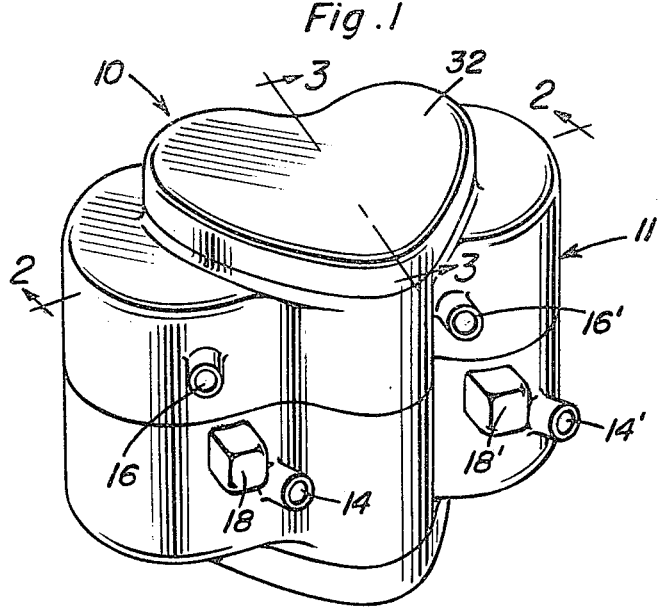
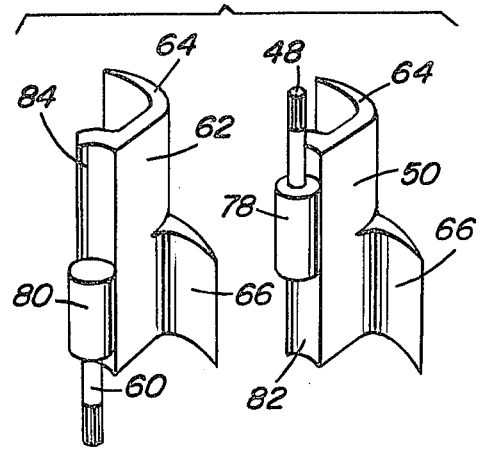
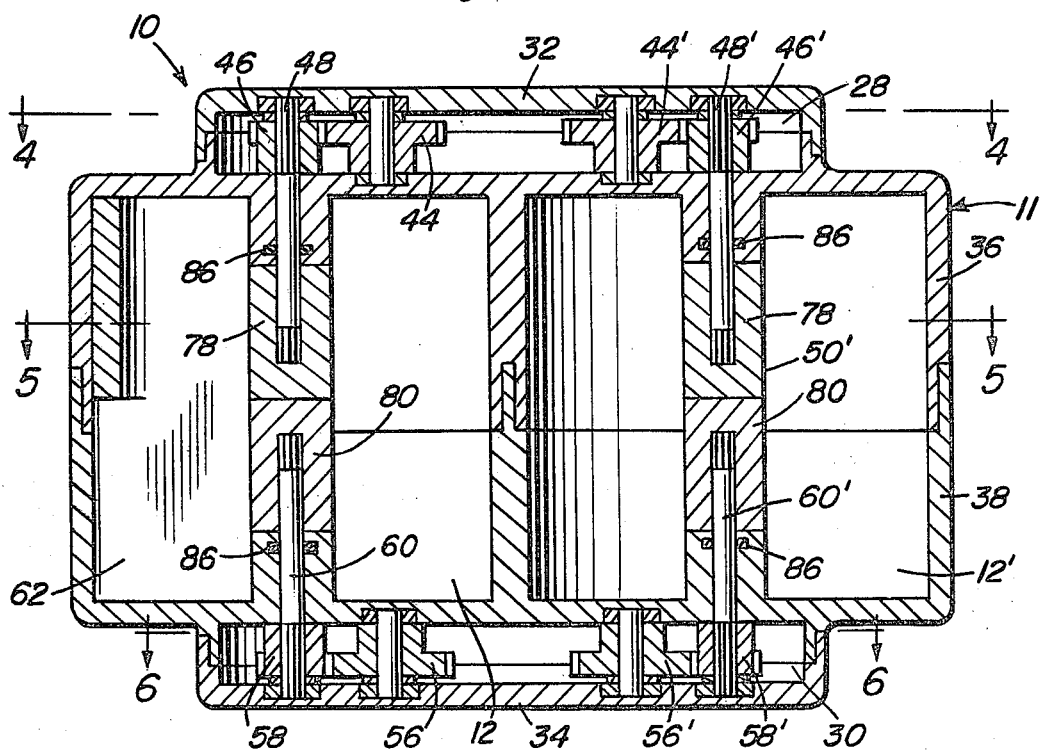
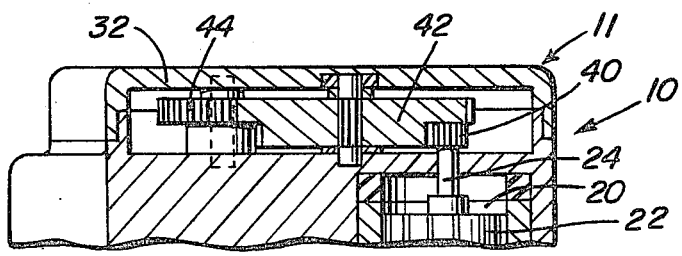

ARTIFICIAL HEART PUMP

BACKGROUND OF THE INVENTION

1. Field of the Invention

The present invention relates to an artificial heart pumping apparatus which may be used either externally or internally of the human body for maintaining life supporting circulation.

2. Description of the Prior Art

Numerous approaches are currently being used either to assist or replace diseased hearts. Included among these is the total replacement of the human heart with an artificial heart pump. Research in this area is being done worldwide, and a variety of functional designs now exist. Unfortunately, these artificial hearts have proven to be unsatisfactory due to one or more of the following factors:

(1) excessively large size or weight, preventing implantation in the chest of pumps which supply both systemic and pulmonary circulation;
(2) non-physiologic cardiac output;
(3) presence of non-pulsatile flow, current research suggesting that pulsatile flow may be beneficial to the organism;
(4) use of heart valves which (a) create turbulence leading to excessive hemolysis, (b) provoke thrombus formation and emboli, and (c) allow the formation of bacterial growth;
(5) presence of recesses, cavities, or areas of blood stagnation which are conducive to bacterial growth and the formation of clots;
(6) lack of sufficiently large atrium resulting in venous hypertension due to decreased diastolic filling;
(7) lack of sufficient control mechanisms for the regulations of cardiac output;
(8) non-equal output into the systemic and pulmonary circulation systems resulting in overload.

A variety of prior art rotating vane pumps do exist. Included among these are the following U.S. patents:

| | | |
|---|---|---|
| 951,197 | O'Connor | Mar. 8, 1910 |
| 7,751 | Davis | Nov. 5, 1850 |
| 1,739,104 | Tropp | Dec. 10, 1929 |
| 2,180,851 | Rosner | Jan. 28, 1938 |
| 2,531,903 | Berck | Nov. 28, 1950 |
| 3,099,260 | Birtwell | July 30, 1963 |
| 3,227,090 | Bartolozzi | Jan. 4, 1966 |
| 3,398,643 | Schudt | Aug. 27, 1968 |

None of the above listed prior art devices, however, recognizes the value of such a rotating vane pump as a substitute for the human heart. Also, the problems inherent in adapting such a pump for use within a human body are neither recognized nor dealt with in these references.

SUMMARY OF THE INVENTION

The human body can be thought of as containing two separate circulations: a right or pulmonary circulation and a left or systemic circulation. These two circuits are intricately connected and interdependent, but due to the nature of human circulation, each requires its own pumping device. Also, since the amount of space in the chest cavity for implantation of an artificial device is limited, it becomes desirable to power both of these pumps with the same drive system. Furthermore, the drive system must conform to the characteristics of the human dual circulation system, the output requirements of which vary continuously with time. Thus, a viable pumping system must be capable of sensing changes in output requirements and must be capable of varying its output so as to keep pace with these changes. In addition, although the pump outputs into the left and right circulations are identical over any short period of time, the instantaneous output of the two circulations at any particular point in time will not necessarily be the same. Therefore, each pump must be able to sense and vary its output independent of the actions of the other pump.

An additional problem relates to the characteristics of the fluid, viz. blood which is to be used in the pump. When blood comes into contact with a rough or foreign surface, it clots. If the clots formed happen to break loose and enter into the systemic circulation, the results could be tragic. In order to prevent or minimize as much as possible these complications, it is necessary to provide a pump mechanism which includes smooth contact surfaces, reduces the presence of recesses or crypts and incorporates a vane motion which insures adequate washing of all pump surfaces.

Accordingly, one object of the present invention is to provide an artificial heart pump which uses two parallel, cylindrical pump chambers with each chamber having a pair of radially extending rotatable pump vanes which are individually, intermittently operated by a single drive motor with the speed of rotation of each vane being individually adjustable in accordance with the volume of blood entering the pump chamber in which that vane is located.

A further object of the present invention is to provide an artificial heart pump wherein the aforementioned rotating vanes include free ends which contact the interior wall of the cylindrical pump chamber and include circumferentially extending baffles which serve to close off the intake and exhaust ports of the pump in order to eliminate the necessity for separate valving mechanisms. The baffles also provide a wiping action along the internal surface of the pump chamber thereby inhibiting the formation of blood clotting.

These, together with other objects and advantages which will become subsequently apparent, reside in the details of construction and operation as more fully hereinafter described and claimed, reference being had to the accompanying drawings forming a part hereof, wherein like numerals refer to like parts throughout.

BRIEF DESCRIPTION OF THE DRAWINGS

FIG. 1 is a perspective view of the artificial heart pump.

FIG. 2 is an elevational sectional view taken substantially along a plane passing through section line 2—2 of FIG. 1 and shows the two parallel chambers.

FIG. 3 is a side elevational view taken substantially along a plane passing through section line 3—3 of FIG. 1 and shows a portion of the drive mechanism for the pump vanes.

FIG. 7 is a perspective view of one pair of radial pump vanes.

DESCRIPTION OF THE PREFERRED EMBODIMENT

Figure 4:
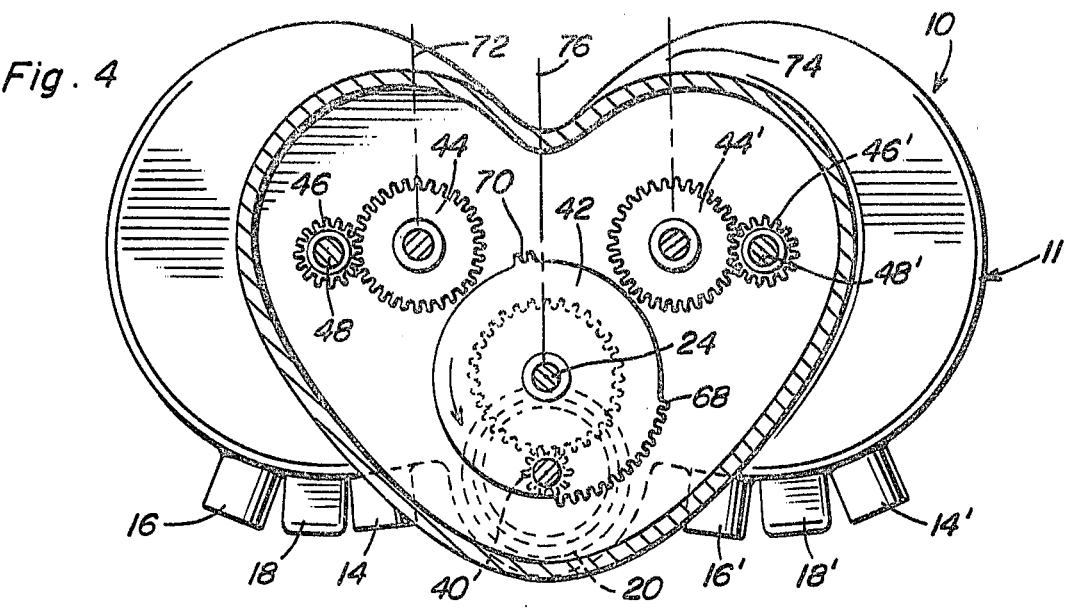
FIG. 4 is a plan sectional view taken substantially along a plane passing through section line 4—4 of FIG. 2 and shows one portion of the drive mechanism for the pump vanes.

Now with reference to the drawings, the artificial heart pump generally referred to by the numeral 10 shall be set forth in detail.

With specific reference to FIGS. 1-6, it will be seen that the artificial heart pump includes a housing 11 enclosing a pair of cylindrical pump chambers 12 and 12'. The pump chambers have, respectively, inlet ports 14 and 14' and exhaust ports 16 and 16'. Located near the inlet ports 14 and 14' are sensors 18 and 18'. Located between and forward of the chambers is the motor cavity 20 which houses drive motor 22. The drive motor has an axially upward extending shaft 24 and downwardly extending shaft 26 which extend respectively into gear housing openings 28 and 30. Separate housing covers 32 and 34 are provided for enclosing the openings 28 and 30 and allowing access thereto. The chamber enclosing portion of housing 11 is divided into an upper portion 36 and a lower portion 38 to provide for access to the interior of the chambers and facilitate in the assembly of the pump.

Upwardly extending motor shaft 24 is attached to pinion gear 40 which drives upper main drive gear 42. Upper drive gear 42 is connected to upper idler gears 44 and 44' which in turn drive upper vane gears 46 and 46'. Vane gears 46 and 46' are respectively connected to upper vane drive shafts 48 and 48' which in turn rotate upper vanes 50 and 50'.

In like manner, downwardly extending motor shaft 26 has attached thereto lower pinion gear 52 which is connected to lower main drive gear 54 which in turn rotates lower idlers 56 and 56' which control lower vane gears 58 and 58' which are respectively attached to lower vane shafts 60 and 60' for effecting rotation of the lower vanes 62 and 62'.

Figure 5:
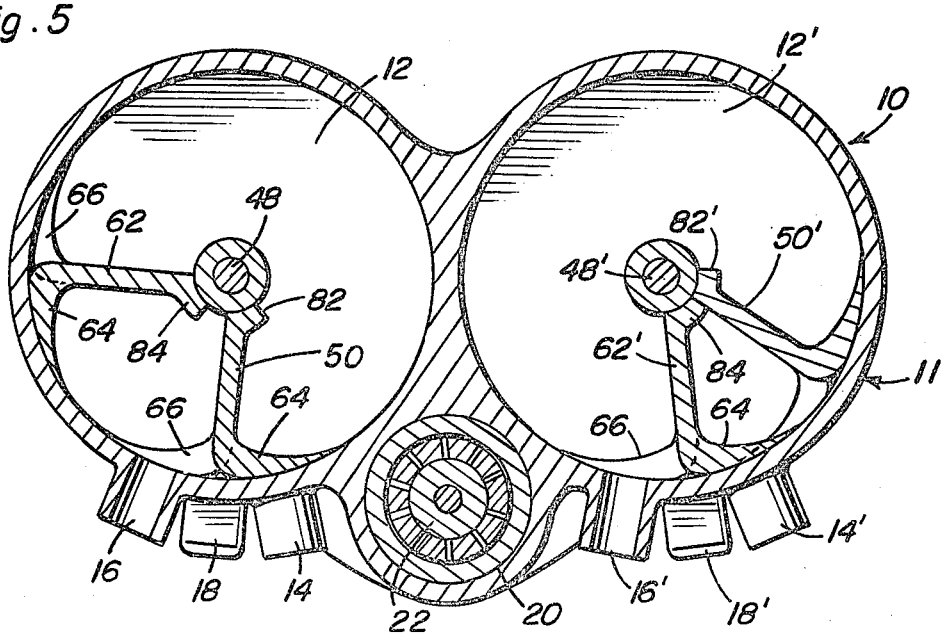
FIG. 5 is a plan sectional view taken substantially along a plane passing through section line 5—5 of FIG. 2 and shows the parallel pump chambers with the radial vanes.

As can be seen in FIG. 7, the vanes 50, 50', 62 and 62' are identical in construction except that the upper vanes have upwardly extending shafts 48 and 48' while the lower vanes have downwardly extending shafts 60 and 60'. With reference to FIGS. 5 and 7, it will be seen that each vane includes a pair of oppositely directed circumferentially extending upper and lower wings labelled 64 and 66, respectively, which contact the internal cylindrical surface of the pump chamber in which the vane is located. These wings serve to wipe the cylindrical walls of the pump chamber to maintain continuous movement of the blood to insure that no clotting will initiate. Furthermore, these wings serve as valves to make sure that no communication between the inlet and exhaust ports of each pump chamber will develop during rotation of the vanes. With the vanes in their initial position, as seen with respect to vanes 50 and 62' in FIG. 5, the wings are positioned such that wings 64 are above inlet ports 14 and 14' and while wings 66 are below the exhaust ports 16 and 16' thus allowing blood to enter and exit from the pump chamber. As shown, vane 62 is rotating in a counter clockwise direction within chamber 12 thereby forcing blood from exhaust port 16 which is positioned between moving vane 62 and stationary vane 50. At the same time, blood enters the chamber through inlet 14 by the sucking action created by moving vane 62 together with natural passive, diastolic action. When vane 62 reaches a position 310 degrees through its arc of rotation, rotation of vane 50 initiates. With both vanes rotating at this time, wing 64 of vane 62 serves to close exhaust port 16 during the major portion of the vane's final 50 degrees of movement. Simultaneously, wing 66 of vane 50 closes inlet port 14 until that vane has reached a position approximately 50 degrees into its arc of rotation. Once vane 62 reaches its initial position spaced midway between the inlet and exhaust port, vane 50 stops at a position 50 degrees into its arc of travel. During movement of vanes 50 and 62, vanes 50' and 62' remain stationary in the position shown. As soon as vanes 50 and 62 come to rest, vane 50' rotates through its arc of movement causing pumping action as described with reference to chamber 12. When vane 50' reaches a position 310 degrees through its arc, both vane 50' and vane 62' move forward and come to rest with vane 62' stopped at a position 50 degrees through its arc of rotation whereupon movement of the vanes in chamber 12 resumes. This intermittent pumping action of each chamber continues indefinitely with the speed of rotation of the vanes being controlled by sensors 18 and 18' as will be described hereinafter.

Figure 8:
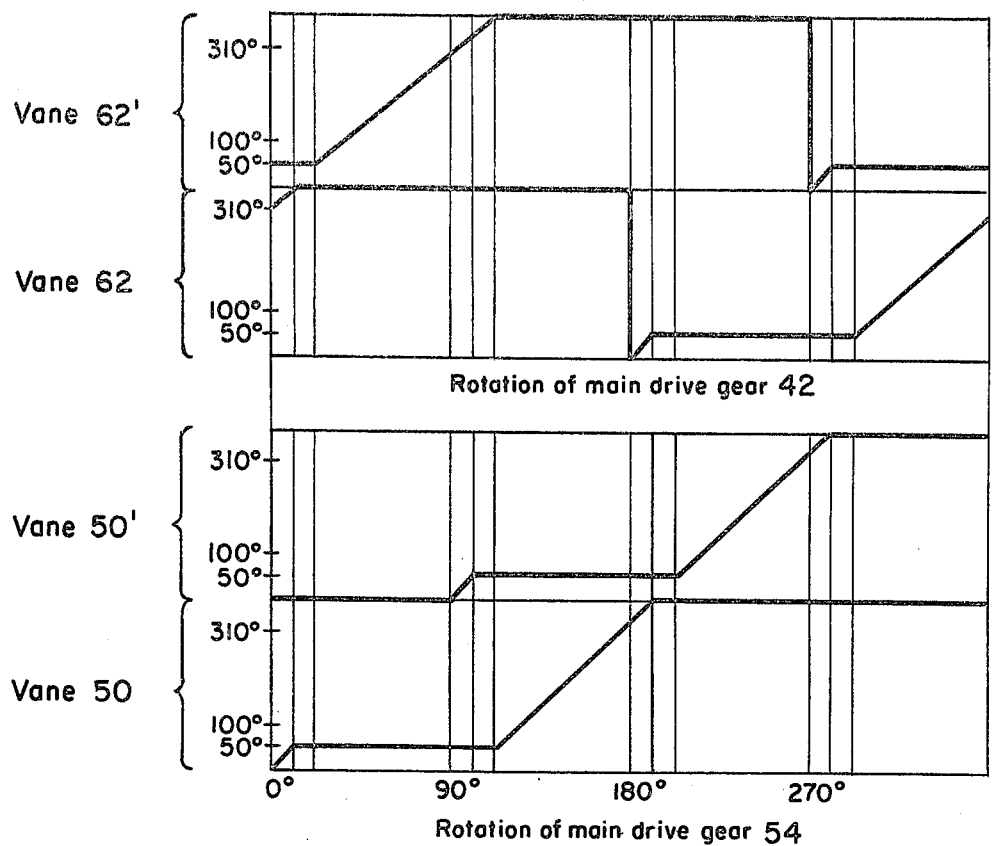
FIG. 8 is a graphical representation demonstrating the relative positions of the four radial pump vanes during operation of the artificial heart pump.

Again with reference to FIGS. 4-6, it can be seen that the intermittent vane motion is produced through the upper and lower main drive gears 42 and 54 by the proper tooth configuration, placement and dimensioning of these gears. The upper and lower gearing arrangements are identical except that main drive gears 42 and 54 are offset by 180 degrees from each other. Therefore, the configuration of these gears will be described only with reference to upper gear 42 and its associated gear works. Gear 42 has a dimension twice that of idler gears 44 and 44' which in turn are twice the diameter and contain twice the number of teeth as gears 46 and 46'. Furthermore, the axes of gears 44 and 44' are offset by 90 degrees from each other with respect to the axis of gear 42. Gear 42 has two sets of offset gear teeth disposed thereon. The first set, generally referred to by the numeral 68, extends for 77.5 degrees about the periphery of gear 42. Thus, when teeth 68 mesh with the teeth of gears 44 or 44', they cause a rotation of 155 degrees which in turn cause gears 48 or 48' to rotate through 310 degrees, rotating their respective vanes therewith. The second teeth set is generally referred to by the numeral 70 and extends for 12.5 degrees about the periphery of gear 42. Teeth 70 terminate at a position 180 degrees offset from the termination of gear teeth 68. Accordingly, teeth 70 cause a final rotation of gears 46 and 46', and their respective vanes, of 50 degrees. The 90 degree offset, discussed above, provides for the sequential action of the vanes contained in the separate pump chambers. The exact input and output vane movements and the temporal relationships produced by this drive system are shown graphically in FIG. 8. The graph plots the degree by degree movement of all four vanes during one complete cycle of the system. FIG. 8 clearly demonstrates the intermittent, sequential movement of the vanes necessary to produce the proper pumping action required. While the gearing system described is actually a modified Geneva-type mechanism, a modified Ferguson drive system may alternately be employed to insure reliability and accuracy of the drive mechanism.

Control of the cardiac output is achieved as a result of Sterling's law of the artificial heart, which states that cardiac output is equal to cardiac input. Thus, if venous pressure is low, the control mechanism is used to effect a change in the rate of rotation of the vanes. Sensors 18 and 18' are positioned proximate the inlet ports and may be pressure responsive sensors. These sensors provide an indication of the amount of blood flowing into the pump chamber. The sensors are connected through a standard electronic speed control circuit to the drive motor 22 so as to vary the speed of that motor in accordance with the amount of blood flowing into the chamber. This arrangement insures that the rate of flow out of the pump is equal to the rate of flow into the pump. Thus, if blood returning to the pump decreases, the mechanism senses a decreased inflow to the chamber and causes a decrease in motor and vane speed. This decreases pump output proportionately to the decrease in pump return until a new steady state is reached. An analogous situation would result if blood returned to the pump increased. In this circumstance, the appropriate sensor would indicate an increase in pressure and cause a corresponding increase in motor speed.

Figure 6:
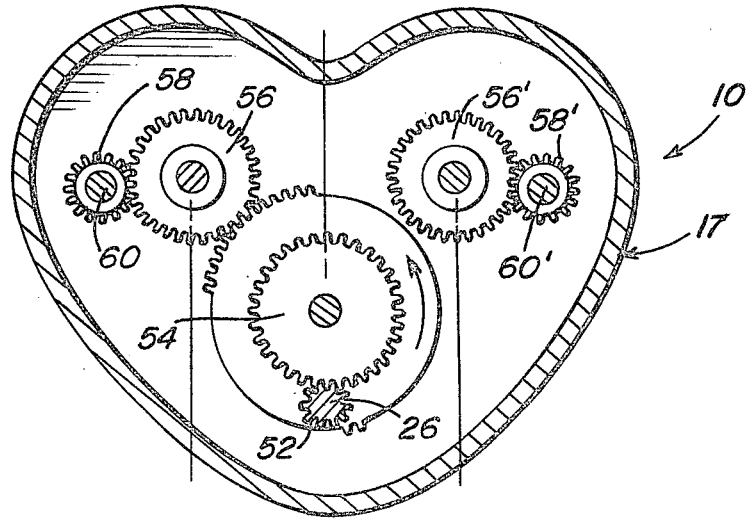
FIG. 6 is a plan sectional view taken substantially along a plane passing through section line 6—6 of FIG. 2 and shows the remainder of the gear drive mechanism.

Naturally, this speed control of the drive motor must be responsive alternately to sensors 18 or 18' dependent upon which pumping chamber is active. This separate control action of the vane speed is accomplished by wiring the sensor circuit through the gearing system of the drive mechanism. This will be described with reference to FIG. 4, bearing in mind that the contacts are identical in the lower gearing system shown in FIG. 6. In FIG. 4 it should be understood that the teeth of gears 44 and 44' are electrically conductive and connected to wires 72 and 74 respectively through slip rings or any other suitable means. Wire 72 is connected to the output of sensor 18 while wire 74 is connected to the output of sensor 18'. Wire 76 is connected to teeth 68 through slip rings or any other suitable means and extends to the motor control circuit. Thus, when the pump chamber 12 is active, electrically conductive teeth 68 engage the teeth of gear 44', thus providing a signal from sensor 18' to the motor control circuit for controlling the speed of motor 22 in response to the pressure within chamber 12'. A similar control is effected for chamber 12 when teeth 68 engage gear 44. Since the teeth on gear 54 shown in FIG. 6 are offset by 180 degrees from teeth 68, alternate control of the motor between the upper and lower drive mechanisms will be effected. Thus, it can be seen that control of the vane in motion in any particularly time will be effected through the sensor located in the chamber in which the vane is rotating.

As mentioned hereinabove, the vanes as shown most clearly in FIGS. 2, 5 and 7, include wings for washing the internal surface of the pump chambers. Furthermore, vanes 50 and 62 include enlarged shaft portions 78 and 80 which are disposed in axial alignment and have contiguous axial faces. As can be discerned from FIG. 7, the inner portion of the vanes 50 and 62 have integral arcuate flanges 82 and 84 respectively which are concentric with the enlarged shaft portion. These arcuate flanges serve to wash the outer periphery of the enlarged shaft portions. For instance, flange 82 is concentric with enlarged shaft portion 78 and washes the external surface thereof to inhibit the formation of blood clots thereon. Furthermore, the outer axial faces of each vane serve to wash the axial surfaces of each pump chamber.

Several additional features of the pump design are incorporated for the purpose of inhibiting clot formation. Also with reference to FIGS. 2 and 7, it can be seen that with the use of the opposed axially extending vane shafts 48, 60 and 48', 60', there is no need to have one shaft rotate inside of the other. Sealing of each shaft with the housing is accomplished by grinding the shaft and the housing surfaces together so as to mate the surfaces. This produces an effectively perfect seal without the necessity of using actual sealing devices and thus eliminates the nidus for thrombus formation. As a safeguard, a spring ring seal is also employed in each mounting boss as shown at 86. It will also be noted that the bosses in which the O-rings are contained are also washed by the arcuate flanges of the vanes. In this manner, by the use of mounting bosses, rather than having the shaft housing interfaced directly with each vane, the sealed space on the shaft can also be swept clean by the arcuate flanges with each revolution of the vane. Finally, it will be noted that the front edge of each arcuate flange comes into contact with the trailing edge of the other vane when the vanes are at rest as shown in FIG. 5 with respect to the vanes of chamber 12'. In this manner, each arcuate flange may clip off any clot formation which may have formed under the flange itself.

Figure 9:
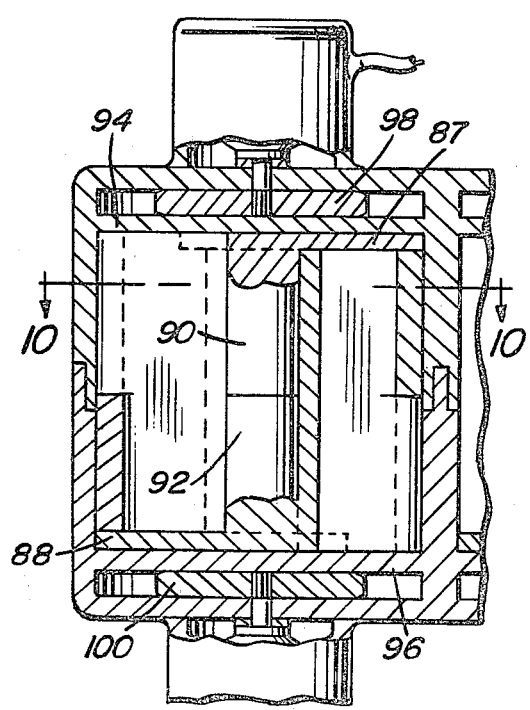
FIG. 9 is an alternate embodiment of the artificial heart pump using shaftless radial rotating vanes.
Figure 10:
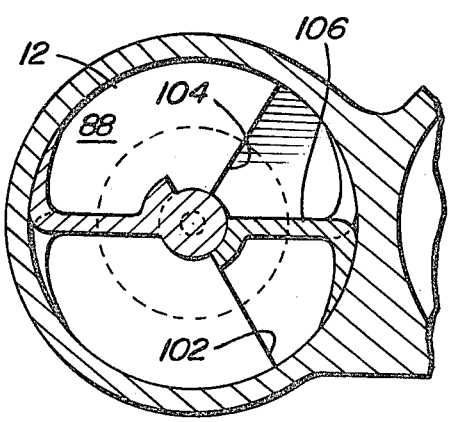
FIG. 10 is a plan sectional view taken substantially along a plane passing through section line 10—10 of FIG. 9.

An alternative embodiment, shown in FIGS. 9 and 10, for the drive mechanism may be used to overcome the problems associated with the use of vane shafts. The embodiment shown in FIGS. 9 and 10 incorporate a magnetically coupled drive system wherein each vane is shaped similarly to those shown in FIG. 7, the major difference being that each vane has a disc portion 87 and 88, respectively. Of course, the enlarged center shaft portion, designated by 90 and 92, respectively, extend all the way to and meet with the discs 87 and 88, respectively. The discs 87 and 88 face opposite axial walls 94 and 96 of the pump housing. In opposed relationship to the disc are drive magnets 98 and 100, respectively. Thus, it can be seen that as the magnets 98 and 100 are driven, as shown in FIG. 9, by separate motors, or by a similar gearing arrangement to that shown in FIGS. 4–6, the magnetic attraction of the magnets to the discs will cause rotation thereof also.

Each of the discs 87 and 88 are identical and include a cut-out section 102 as shown in FIG. 10 and included in disc 88. Cut-out portions 102 and 104 are included in the disc 88 on each side of vane 106 to which these discs are attached. These cut-outs are for the purpose of providing scraping action along the axial wall of the chamber to which the disc is adjacent. The exact size of the disc will correspond to the exact size of the angle subtended by the independent movement of one vane. Thus, the disc itself will encompass 260 degrees.

The foregoing is considered as illustrative only of the principles of the invention. Further, since numerous modifications and changes will readily occur to those skilled in the art, it is not desired to limit the invention to the exact construction and operation shown and described, and accordingly all suitable modifications and equivalents may be resorted to, falling within the scope of the invention.

What is claimed as new is as follows:

1. An artificial heart pump for use in replacing the natural heart organ comprising: a first pumping mechanism including a first cylindrical pump chamber and including a first pair of independently rotatable radially extending pump vanes mounted in said first pump chamber; a first inlet means and a first outlet means for connecting said first pump chamber to a systemic circulatory system; a second pumping mechanism including a second cylindrical pump chamber, a second pair of radially extending rotatable vanes mounted in said second pump chamber, a second input means and a second output means for connecting said second pump chamber to a pulmonary circulatory system; drive means connected to said first pair of radially extending vanes and said second pair of radially extending vanes for causing independent rotation of said first pair of radially extending vanes and said second pair of radially extending vanes; and control means for controlling the operation of said drive means for equalizing the input and output of each of said pumping mechanisms.

2. The artificial heart pump of claim 1 wherein said drive means includes a motor connected to a gear means for providing sequential operation of said first pair of radially extending vanes and said second pair of radially extending vanes.

3. The artificial heart pump of claim 2 wherein said gear means includes a first main drive gear and a second main drive gear, each of said first and second main drive gears being in operative engagement with a first and second vane drive gear with each of said vane drive gears being connected to a separate one of said radially extending vanes, each of said main drive gears having a selective engagement means incorporated thereon for providing sequential actuation of said first and second vane drive gears.

4. The artificial heart pump of claim 3 wherein said first and second main drive gears are identical in configuration and offset by 180 degrees from each other.

5. The artificial heart pump of claim 1 wherein each of said radially extending vanes includes a chamber wiping means for wiping the internal surfaces of said cylindrical pump chamber to inhibit the formation of blood clots.

6. The artificial heart pump of claim 5 wherein said chamber wiping means engages said input and output means for selectively closing off said input and output means.

7. The artificial heart pump of claim 6 wherein said chamber wiping means includes a pair of oppositely directed, circumferentially extending, axially spaced elements which engage the inner circumferential surface of said cylindrical pump chamber.

8. The artificial heart pump of claim 5 wherein each of said radially extending vanes further includes a vane wiping means for wiping a portion of the other vane of each of said pair of vanes for inhibiting the clotting of blood thereon.

9. The artificial heart pump of claim 1 wherein said control means includes a first pressure sensor located in said first cylindrical pump chamber for providing a signal indicative of the pressure therein, and a second pressure sensor located in said second cylindrical pump chamber for providing a signal indicative of the pressure therein.

10. The artificial heart pump of claim 9 wherein said control means further includes a speed control means for controlling the speed of said drive means, said speed control means being selectively engageable to either said first pressure sensor or said second pressure means.

11. The artificial heart pump of claim 1 wherein said drive means includes a magnetic coupling means for producing rotation of said first and second pair of vanes.

12. the artificial heart pump of claim 11 wherein said magnetic coupling includes a disc segment connected to each of said radially extending vanes; and a rotatable magnetic element associated with each said disc segment disposed externally of said pump chamber for magnetically attracting the associated disc segment.

13. The invention as defined in claim 12 wherein said drive means further includes a separate motor associated with each of said rotatable magnets.

14. An artificial heart pump for providing separate pumping mechanisms for the systemic and pulmonary circulation systems of the human body comprising:

first pumping means, including a first cylindrical pump chamber having an input port and an output port, for causing a pumping of blood through the systemic circulation system of the human body said first pumping means including a pair of independently rotatable radially extending vanes:

second pumping means, including a second cylindrical pump chamber having an input port and an output port, for causing a pumping of blood through the pulmonary circulation system of the human body said second pumping means including a second pair of independently rotatable radially extending vanes;

motor means for providing mechanical power to each of said first and second pumping means;

gear means for connecting said power means to said first and second pumping means for delivering power to said pumping means to cause individual, sequential operation of said first and second pumping means;

first sensor means connected to said first pumping means for causing the first pumping means outflow rate to be equal to the first pumping means inflow rate; and second sensor means connected to said second pumping means for causing the second pumping means outflow rate to be equal to the second pumping means inflow rate.

15. The artificial heart pump of claim 14, and further wherein each of said vanes includes an input valving extension and an output valving extension for covering and uncovering said input and output ports.

16. The artificial heart pump of claim 15 wherein said input valving extensions and said output valving extensions contact their respective pump chamber walls for causing a wiping action on said walls to inhibit the formation of blood clots.

17. The artificial heart pump of claim 14 wherein said first and second sensor means are individually connected to control the speed of said motor means when said gear means is providing power to their respective pumping means.

18. The artificial heart pump of claim 14 wherein said first and second sensor means comprise pressure sensors.

* * * * *